US008701674B2

(12) United States Patent
Tweardy et al.

(10) Patent No.: US 8,701,674 B2
(45) Date of Patent: Apr. 22, 2014

(54) IMMOBILIZATION DEVICE

(75) Inventors: Lisa Tweardy, Moorestown, NJ (US);
Jeff Nemeth, Chandler, AZ (US);
Yessenia Lopez, Cypress, CA (US);
Scott Alan Allread, Marshall, MI (US);
Joseph Marlin Shook, II, Concord, MI (US)

(73) Assignee: Ossur HF, Reykjavik (IS)

( * ) Notice: Subject to any disclaimer, the term of this patent is extended or adjusted under 35 U.S.C. 154(b) by 70 days.

(21) Appl. No.: 12/760,887

(22) Filed: Apr. 15, 2010
(Under 37 CFR 1.47)

(65) Prior Publication Data

US 2011/0118639 A1     May 19, 2011

Related U.S. Application Data

(63) Continuation-in-part of application No. 12/617,819, filed on Nov. 13, 2009, now Pat. No. 8,356,604.

(51) Int. Cl.
*A61F 5/37* (2006.01)

(52) U.S. Cl.
USPC ............. 128/870; 128/869; 128/874; 602/17; 602/18

(58) Field of Classification Search
USPC ........ 602/5, 17–20, 36–37, 32; 128/870, 874, 128/869, 846; 606/286, 289; 2/462, 102, 2/126, 467, 113, 455–456, 459, 463–464
See application file for complete search history.

(56) References Cited

U.S. PATENT DOCUMENTS

| | | |
|---|---|---|
| 2,166,229 A | 7/1939 | Anderson |
| 2,474,200 A | 6/1949 | McBee |
| 2,706,982 A | 4/1955 | Hale et al. |
| 2,828,737 A | 4/1958 | Hale |
| D186,642 S | 11/1959 | Hale |
| 2,973,030 A | 2/1961 | Matthewson |
| 3,601,123 A | 8/1971 | McFarland |
| 3,605,736 A | 9/1971 | D'Amico et al. |
| 3,724,452 A | 4/1973 | Nitschke |
| 3,795,243 A | 3/1974 | Miller |
| 3,799,156 A | 3/1974 | Gurkin |
| 3,827,429 A | 8/1974 | Heikes |
| 3,945,376 A | 3/1976 | Kuehnegger |
| D245,537 S | 8/1977 | Gurgiolo |
| 4,194,501 A | 3/1980 | Watt |
| 4,383,523 A | 5/1983 | Schurman |

(Continued)

OTHER PUBLICATIONS

Brown et al., Atlas of Orthoses and Assistive Devices, Chapter 13, Orthoses for Spinal Trauma and Postoperative Care, pp. 251-258, 1997.

*Primary Examiner* — Tatyana Zalukaeva
*Assistant Examiner* — Camtu Nguyen
(74) *Attorney, Agent, or Firm* — Workman Nydegger

(57) ABSTRACT

An immobilization device including an anterior component including a two-dimensional shaped section contoured to a shape of the human chest and an anterior outwardly bowed area relative to the two-dimensional shaped anterior section generally corresponding to the sternum of the wearer. The device also includes a posterior component including a two-dimensional shaped section contoured to a shape of the human back and a posterior outwardly bowed area relative to the two-dimensional shaped section corresponding to the spinal column of the wearer, with elongate cushion elements connected to and extending within a width of the posterior outwardly bowed area. A strapping system connects both the anterior and posterior components to one another.

11 Claims, 13 Drawing Sheets

(56) References Cited

U.S. PATENT DOCUMENTS

| | | | |
|---|---|---|---|
| D277,236 S | 1/1985 | Gregory | |
| 4,502,471 A | 3/1985 | Owens | |
| 4,515,153 A | 5/1985 | Calabrese | |
| 4,520,801 A | 6/1985 | Lerman | |
| 4,539,979 A | 9/1985 | Bremer | |
| 4,541,421 A | 9/1985 | Iversen et al. | |
| D286,073 S | 10/1986 | Russell | |
| 4,620,530 A | 11/1986 | Lanier et al. | |
| 4,628,913 A | 12/1986 | Lerman | |
| 4,632,099 A | 12/1986 | Mollo | |
| 4,677,969 A | 7/1987 | Calabrese | |
| 4,732,144 A | 3/1988 | Cunanan | |
| 4,751,923 A * | 6/1988 | Marino | 602/4 |
| D296,595 S | 7/1988 | Flosi et al. | |
| 4,776,327 A | 10/1988 | Russell | |
| 4,807,605 A | 2/1989 | Mattingly | |
| D302,308 S | 7/1989 | Russell | |
| 4,913,135 A | 4/1990 | Mattingly | |
| D311,608 S | 10/1990 | Harding | |
| 5,121,741 A * | 6/1992 | Bremer et al. | 602/18 |
| 5,171,296 A | 12/1992 | Herman | |
| D340,784 S | 10/1993 | Clayton | |
| 5,261,873 A * | 11/1993 | Bremer et al. | 602/32 |
| 5,531,669 A | 7/1996 | Varnau | |
| 5,564,788 A | 10/1996 | Warhaftig | |
| 5,865,780 A | 2/1999 | Tuite | |
| 5,964,722 A | 10/1999 | Goralnik et al. | |
| 5,978,961 A * | 11/1999 | Barker | 2/2.5 |
| 6,021,528 A * | 2/2000 | Jurga et al. | 2/326 |
| 6,315,746 B1 | 11/2001 | Garth et al. | |
| 6,347,406 B1 * | 2/2002 | Jones et al. | 2/69 |
| 6,663,630 B2 | 12/2003 | Farley et al. | |
| 6,722,077 B2 * | 4/2004 | Heiges | 43/3 |
| D492,819 S | 7/2004 | Beland | |
| 6,921,376 B2 * | 7/2005 | Tweardy et al. | 602/18 |
| D556,383 S | 11/2007 | Petzl | |
| D597,708 S | 8/2009 | Basenberg, Jr. et al. | |
| D600,860 S | 9/2009 | Durham | |
| 2008/0250552 A1 * | 10/2008 | Durham | 2/456 |
| 2010/0298749 A1 | 11/2010 | Garth et al. | |

* cited by examiner

IMMOBILIZATION DEVICE

CROSS-REFERENCE TO RELATED APPLICATIONS

This application is a continuation-in-part of U.S. application Ser. No. 12/617,819, filed on Nov. 13, 2009, now U.S. Pat. No. 8,356,604 the entirety of which is incorporated herein by reference.

FIELD OF THE INVENTION

The present invention relates to an immobilization device for use by wearers having cervical or spinal injuries. Specifically, the immobilization device functions to fully or partially immobilize the head and neck of the wearer by way of vest components for supporting and transferring loads from halo support rods that support a halo about a wearer's head.

BACKGROUND

Immobilization devices, such as halo vests, are used to immobilize cervical and spinal injuries to facilitate healing. The immobilization devices are normally worn for an extended duration as these sensitive injuries heal. A conventional immobilization device includes front and rear vest components connected to one another and secured to the wearer by a plurality of straps. Halo support rods connect to the vest components and support a halo upright assembly that in turn may be secured to the wearer's head in a variety of known configurations.

While there are numerous known immobilization devices, many of these known devices are inadequate at comfortably distributing pressure exerted onto the chest of the wearer from the halo upright assembly. In particular, many conventional devices apply pressure to anatomical regions that are sensitive to loading. These known devices are cumbersome to apply, particularly for weakened wearers, and do not adequately adapt to the anatomy of the wearer. Moreover, known devices are often found to be ill fitting and lack means for adjustment to a variety of anatomical sizes.

Accordingly, exemplary embodiments of an immobilization device are described herein which alleviate or eliminate the above-mentioned drawbacks.

SUMMARY

In accordance with an embodiment of the invention, an immobilization device includes an anterior component defining a two-dimensional shaped section contoured to a shape of the human chest. The anterior component forms an anterior outwardly bowed area relative to the two-dimensional shaped anterior section and corresponding to the sternum of the wearer. The device also includes a posterior component defining a two-dimensional shaped section contoured to a shape of the human back. The posterior component forms a posterior outwardly bowed area relative to the two-dimensional shaped section corresponding to the spinal column of the wearer. Elongate cushion elements are connected to and generally confined within a width of the posterior outwardly bowed area. A strapping system connects the anterior and posterior components.

The posterior component defines upper and lower portions. The posterior outwardly bowed portion is preferably three-dimensionally shaped relative to the two-dimensional shaped section forming the remainder of the posterior component.

The posterior component may define an elongate opening extending between the upper and lower portions of the posterior component and generally corresponding to the spinal column of the wearer. It follows that two cushion elements are preferably adhered to the posterior component within the posterior outwardly bowed area and on opposed sides of the opening and generally corresponding to sides of the spinal column of the wearer. The cushion elements may be secured at an upper portion of the posterior component, and extend past the posterior bowed area to the lower portion of the posterior component.

The posterior component may define opposed upper arms each having a living hinge such that the strapping system connects to the upper arms and extends over the living hinges. An upper portion of the posterior component defines a posterior curved recess extending laterally across thereof. The immobilization device further includes a posterior cross plate having dimensions corresponding to the posterior recess and arranged to be secured within the posterior recess. The posterior cross plate is contoured to correspond to the posterior bowed area. The immobilization device further comprises an upright halo support having at least two rods securing to opposed ends of the posterior cross plate.

The anterior component defines an anterior curved recess extending laterally across the anterior component, and further includes an anterior cross plate having corresponding dimensions to the anterior recess and arranged to be secured within the anterior recess. The anterior cross plate is preferably contoured to correspond to the anterior outwardly bowed area. An upright halo support having at least two rods may secure to opposed ends of the anterior cross plate.

A lower strapping system includes first and second lower strap stabilizers each having a first end connected to corresponding first and second sides, respectively, of a lower portion of the posterior component. First and second slots are formed on the anterior component for loosely receiving a second end of the first and second lower strap stabilizers, respectively. First and second elastic lower straps each have a first end connected to the first and second lower strap stabilizers at the lower portion of the posterior component, respectively. The lower straps adjustably extend over the first and second lower strap stabilizers and have second ends securable to one another. According to one variation of the strapping system, the second end of each of the lower strap stabilizers is trimmable in length.

The lower strap stabilizers preferably define a retention element near the first end thereof arranged for retaining the chest elastic straps in close proximity therewith on the posterior side of the immobilization device. The lower strap stabilizers may be detachably connected to the posterior component, and the lower strap stabilizers may have greater rigidity than the elastic straps. Furthermore, the second ends of the lower straps can have a plurality of unfixed locations that secure to one another.

The strapping system also includes first and second upper or shoulder strap stabilizers each having a first end connected to corresponding first and second sides, respectively, of an upper portion of the posterior component. First and second upper straps having a first end are connected to the first and second sides of the upper portion of the posterior component, respectively. The upper straps adjustably extend over and beyond the first and second upper strap stabilizers and connect to corresponding first and second sides of an upper portion of the anterior component. The first and second sides of the upper portion of the posterior component each define a living hinge permitting articulation of the upper portion of the posterior upon tensioning of the upper straps.

In another embodiment of the immobilization device, an anterior component defines different portions contoured to a shape of a human chest. The anterior component has an upper portion defining opposed sides each forming a strap receiving anterior tab. Each anterior tab includes a bottom portion extending from an end area of the upper portion, and a top portion defining a slot. The top portion is angled outwardly away from the upper portion so as to extend away from a human chest. A posterior component connects to the anterior component via a shoulder strapping system. The upper strapping system connects the anterior tabs to the posterior component such that when the upper strapping system is tensioned, force is distributed away from a wearer's chest by the anterior tabs.

According to one variation of this embodiment, the anterior tabs rigidly extend from the upper portion of the anterior component. In an alternative variation, the anterior tabs are arranged to resiliently bias outwardly from the upper portion.

An upright halo support having first and second anterior rods may secure to the first and second end areas of the anterior component at anterior locations below the first and second anterior tabs.

In another variation, the anterior location whereat the first and second anterior rods secure is generally located at the same height on a wearer as the posterior location whereat the first and second posterior rods secure. The first and second anterior rods may extend upwardly from the upper portion in alignment with the first and second anterior tabs such that the first and second rods extend past the first and second anterior tabs, respectively, within a width of the first and second anterior tabs, respectively. The first and second posterior rods may likewise extend upwardly from the posterior component in alignment with the first and second posterior tabs such that the first and second posterior rods extend past the first and second posterior tabs, respectively, within a width of the first and second posterior tabs.

In another embodiment of the immobilization device, an anterior component defines portions contoured to a shape of a human chest. The anterior component has a bottom portion defining a central lower region including first and second opposed sides forming first and second belt loops, respectively, protruding outwardly from the bottom portion. First and second wings extend from beyond the corresponding first and second belt loops. The central lower region forms first and second living hinges located near the corresponding first and second belt loops, and the hinges are biased so as to facilitate drawing the first and second opposed sides of the central lower portion inwardly toward one another and against a wearer's abdominal region. It will be understood that this arrangement allows for a more secure fit over the wearer's abdominal or lower chest regions and more effectively distributes pressure exerted on the wearer by the lower strapping system.

In a variation, the lower strapping system includes first and second elongate strap stabilizers mounted on the posterior component, wherein the anterior component has at least one locking aperture formed on the central lower region. A locking device secures the lower strapping system to the anterior component by engaging the locking aperture. The lower strapping system extends over the first and second wings, respectively, and urges the first and second wings inwardly at least at the first and second living hinges.

According to another embodiment, the immobilization device has an anterior component including a two-dimensional shaped section contoured to a shape of the human chest. The anterior component forms an anterior outwardly bowed area relative to the two-dimensional shaped anterior section and corresponds to the sternum of the wearer. The anterior component includes a top component, and a bottom component having a central strut segment extending in a substantially vertical configuration. The top component has a substantially vertical attachment portion slidably engaging the bottom component. The top component defines an upper portion extending inwardly at a transition point toward a wearer at an oblique angle relative to the attachment portion. This arrangement permits the top component to more closely conform to the anatomy of the wearer.

In one variation, the transition point is a living hinge arranged to variably bias the upper portion relative to the attachment portion. In another variation, the transition point rigidly directs the upper portion relative to the attachment portion. A clinician may use the transition point so as to appropriately shape the anterior component according to an individual wearer's anatomy.

BRIEF DESCRIPTION OF THE DRAWINGS

Features, aspects, and advantages of the present invention will become better understood with regard to the following description, appended claims, and accompanying drawings.

DETAILED DESCRIPTION OF VARIOUS EMBODIMENTS

A. Overview

Figure 1A:
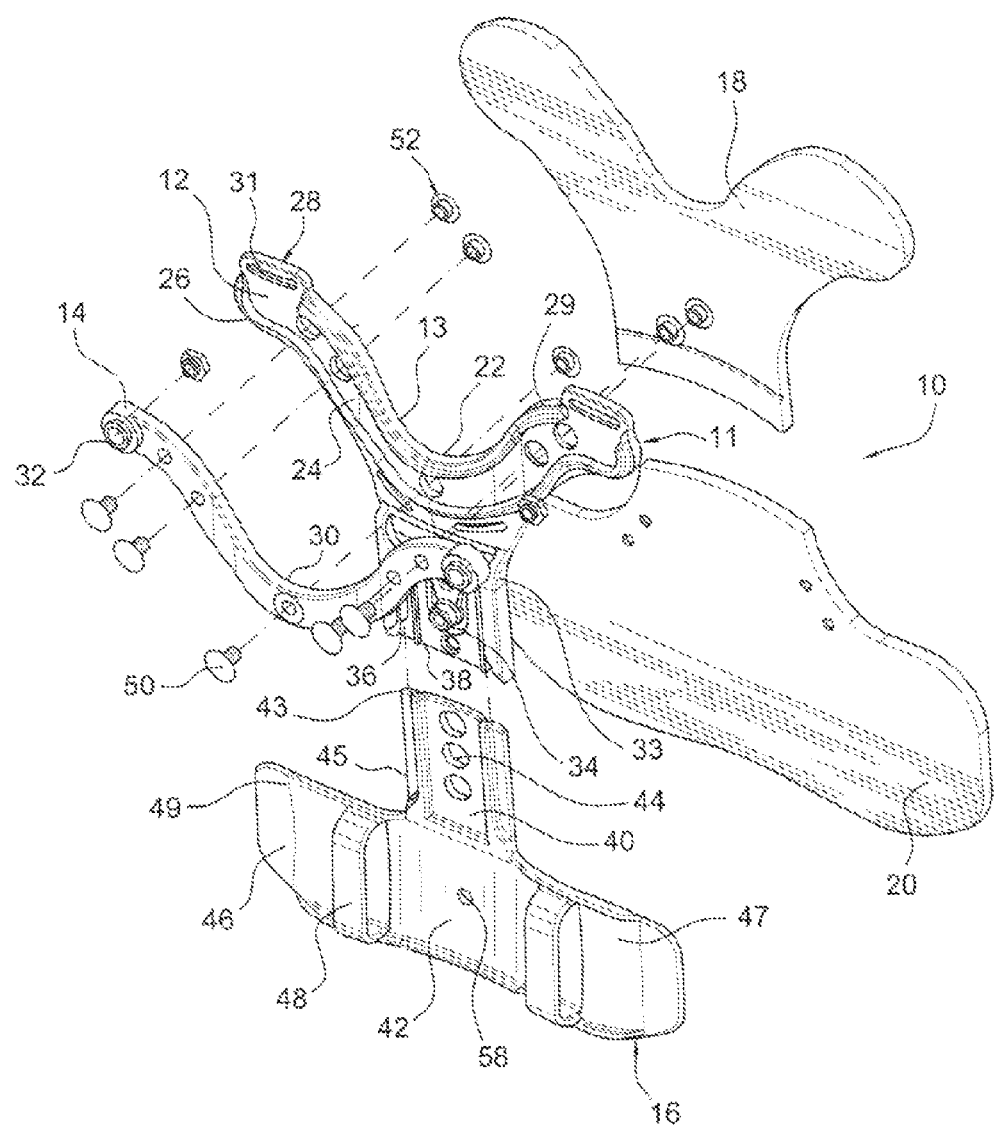
FIG. 1A is an exploded perspective view of an anterior component according to an embodiment of the invention.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning Any element in a claim that does not explicitly state "means for" performing a specified function, or "step for" performing a specific function, is not to be interpreted as a "means" or "step" clause as specified in 35 U.S.C. §112, paragraph 6.

B. Various Embodiments of the Immobilization Device

In general, the immobilization device includes an anterior vest assembly and a posterior vest assembly connecting to the anterior vest assembly via a halo upright assembly and a strapping system. Interface plates form part of the anterior and posterior vest assemblies, and serve as mounting supports for the upright assembly. Suitable padding is provided which corresponds to the anterior and posterior vest assemblies, and secures to rear surfaces thereof and are located adjacent to the body of the wearer.

The anterior and posterior vest assemblies each have a configuration that minimizes pressure on bony prominences of the wearer. Specifically, the contours of the vest assemblies include contoured surfaces at curved bone areas of the wearer, and outwardly bowed areas to minimize pressure at particularly sensitive anatomical regions. Indeed, corresponding vest assemblies cover the sternum but bow outwardly thereat, and partially cover the ribs, but may not directly engage the wearer's shoulder blades, or the spinous processes.

The halo upright is particularly provided to maintain the head of the wearer in a predetermined spatial relationship to the body of the wearer, and includes a plurality of support plates and support rods which couple to the interface plates for securing to the anterior and posterior vest assemblies. The upper strapping system includes adjustable-length flexible straps connecting the vest assemblies at the top or shoulders of the wearer, and a lower strapping system including an adjustable length belt connecting the vest assemblies at the lower portion, or the lower chest or abdominal regions of the wearer.

In view of these basic features of the immobilization device, attention is turned to the individual features of the anterior and posterior vest assemblies.

Figure 2A:
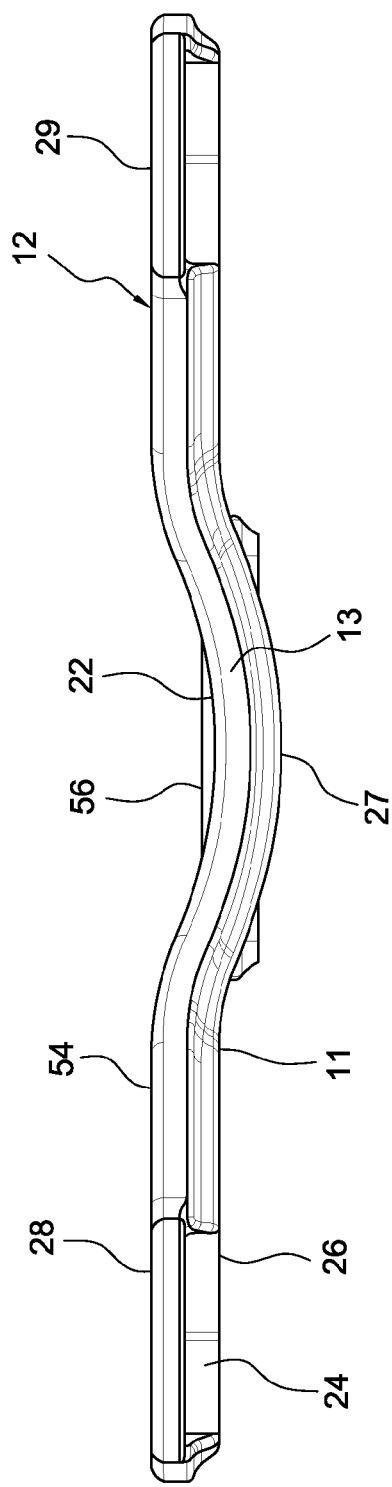
FIG. 2A is a top elevational view showing the anterior top component according to FIG. 1A.

An exemplary anterior vest assembly or component 10 according to the immobilization device of the present invention is shown by way of FIGS. 1A and 2A. The anterior vest assembly 10 includes a top component 11, an interface plate 14 extending laterally across the top component 11, and a bottom component 16 adjustably connected to the top component 11. The top and bottom components 11, 16 may be constructed from a semi-rigid or rigid polymeric material, and may be generally shaped to the contours of a human chest. Padding 18, 20 is provided which lines inner surfaces of the top and bottom components 11, 16, respectively.

The top component 11 has an upper portion 12 including first and second arms 28, 29 separated by a recessed arcuate profile 13 defined therebetween. The region proximate the arcuate profile 13 downwardly extends into the top component 11 and is located between the arms 28, 29 thereby defining a three-dimensionally outwardly bowed portion 22. Thus, where the top component 11 overlies the sternum of the wearer, the bowed portion 22 spaces the top component 11 from the sternum of the wearer. It follows that the top component minimally applies or does not apply any pressure to the area at and immediately surrounding the wearer's sternum.

The three-dimensionally shaped bowed portion 22 is contoured markedly different in contrast to the remainder surfaces 54, 56 of the top and bottom components 11, 16 (shown herein by example in a flat configuration), respectively, which may be considered as being two-dimensionally shaped relative to the bowed portion. The two-dimensional shape in other words is defined as adhering to the generically shaped features of the top and bottom components, whereas the bowed portion protrudes outwardly relative to the remainder surfaces.

The top component 11 defines a curvilinear recess 24 which closely conforms to the shape of the anterior interface plate 14, thereby enabling the interface plate 14 to be securely received therein. As depicted in FIG. 1A, the curvilinear recess 24 and the interface plate 14 likewise are shaped to correspond to the arcuate profile 13. Indeed, the curvilinear recess 24 is formed over at least a portion of the bowed portion 22, and thereby both the curvilinear recess 24 and the interface plate 14 have bowed portions, 27, 30, respectively, which are shaped to likewise protrude outwardly along with the bowed portion 22 of the upper portion 12 relative to the remainder surfaces of the top component 11. The interface plate 14 is secured to the top component 11 via suitable male and female fasteners 50, 52.

A lip 26 protrudes from the top component 11 and extends along upper and lower perimeters of the curvilinear recess 24 so as to retain the interface plate 14 therein. Moreover, the extent at which the lip 26 protrudes outwardly from the top component 11 is preferably the same distance as the thickness as the interface plate 14. Therefore, the interface plate 14 and the lip 26 are flush with one another, thereby providing a relatively smooth combination of surfaces.

There is an absence or interruption of the lip 26 at the top portion of the first and second arms 28, 29. Instead, a slot 31 is formed from the top component and is used to couple with shoulder straps extending from the posterior vest assembly 100. The absence of the lip at the top portion of the first and second arms 28, 29 also allows for attachment points 32 formed at opposed ends of the interface plate 14 to be exposed for coupling to corresponding support rods of the upright assembly.

The top component 11 includes an elongate attachment portion 33 located at a lower portion thereof. While the attachment portion 33 and the bottom component 16 are connected in a similar manner to the subassembly described in U.S. Pat. No. 6,921,376, incorporated herein by reference, there are a few deviations.

The attachment portion 33 includes an affixation point 34 which is a button biased outwardly which locks onto one of a series affixation points 44 defined on a centrally located strut segment 40 formed by the bottom component 16 to secure the top and bottom components together. The series of affixation points 44 permits adjustment of the height position of the bottom component relative to the top component, thereby accommodating patients of different body types. The attachment portion 33 defines opposed laterally extending flanges directed toward the affixation point 44, and sized so as to slidably receive and retain outer edges 45 of the bottom component 16. The attachment portion 33 also defines elongate ribs 38 that are correspondingly received by channels 43 formed on the bottom component 16.

The bottom component 16 defines lateral wings 46, 47 extending from a central lower region 42. The wings 46, 47 are adapted to extend about at least the anterior regions of the wearer's ribs to thereby bear on selected muscle groups. The wings 46, 47 define loops 48, and the central lower region 42 defines an aperture 58. The loops 48 and the aperture 58 are adapted to receive suitable straps or similar affixation elements that permit the anterior and posterior vest assemblies to be comfortably and securely fitted onto the wearer.

In reference to the embodiment depicted in FIG. 1B, a variation of the anterior vest assembly 310 is shown generally having many of the same features as in the embodiment 10 according to FIG. 1A, and additional features described below. The anterior vest assembly 310 is shown with an upright halo support 317 having first and second anterior rods 317A, 317B securing to first and second end areas 359A, 359B of the interface plate 314 on the top component 311 at anterior locations below first and second anterior strap receiving tabs 357 at first and second arms 328, 329, respectively, formed from opposed upper portions of the top component 311.

Figure 2B:
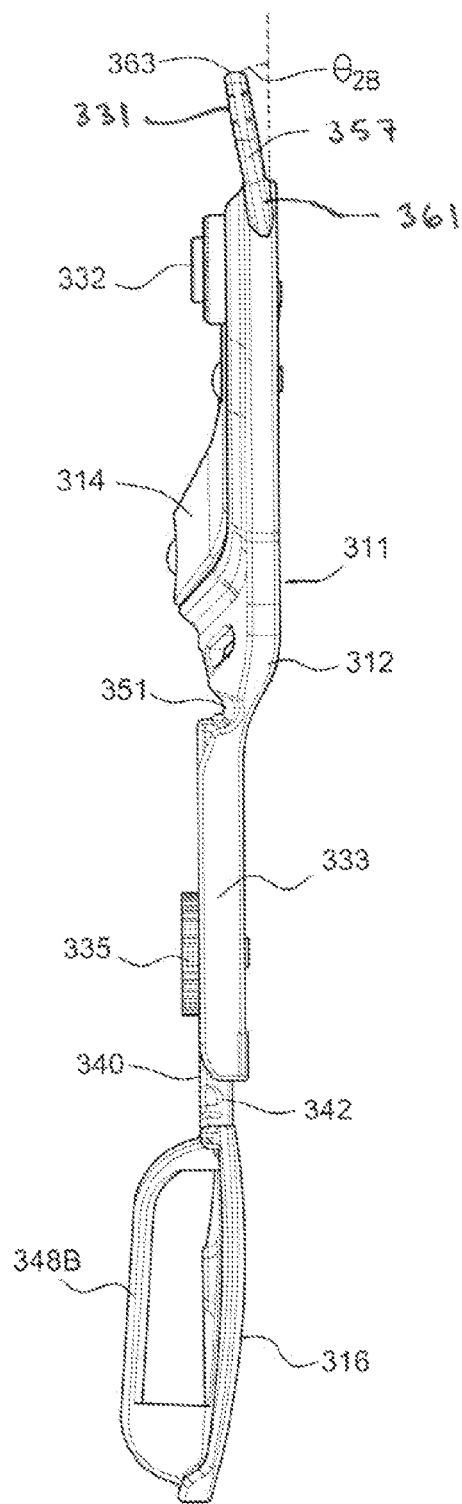
FIG. 2B is a side elevational view showing the anterior component according to FIG. 1B.

Turning to FIG. 2B, the anterior tab 357 includes a bottom portion 361 extending from an end area of the upper portion 312, specifically a top distal edge of the upper portion. The anterior tab 357 has a top portion 363 defining a slot 331 and angled outwardly away from upper portion 312 so as to extend obliquely at angle $\Theta_{2B}$ away from a wearer's chest, in particular at the clavicle portions of the wearer's chest. Because the clavicle is a bony protuberance, the anterior tabs effectively reduce or eliminate undue forces at the clavicle.

A shoulder strapping system connects the anterior tabs to the posterior component such that when the strapping system is tensioned, force is distributed away from a wearer's chest at the at least one anterior tab.

According to one variation, the anterior tabs rigidly extend from the upper portion of the anterior component. In another variation, the anterior tabs resiliently extend from the upper portion of the anterior component.

Figure 1B:
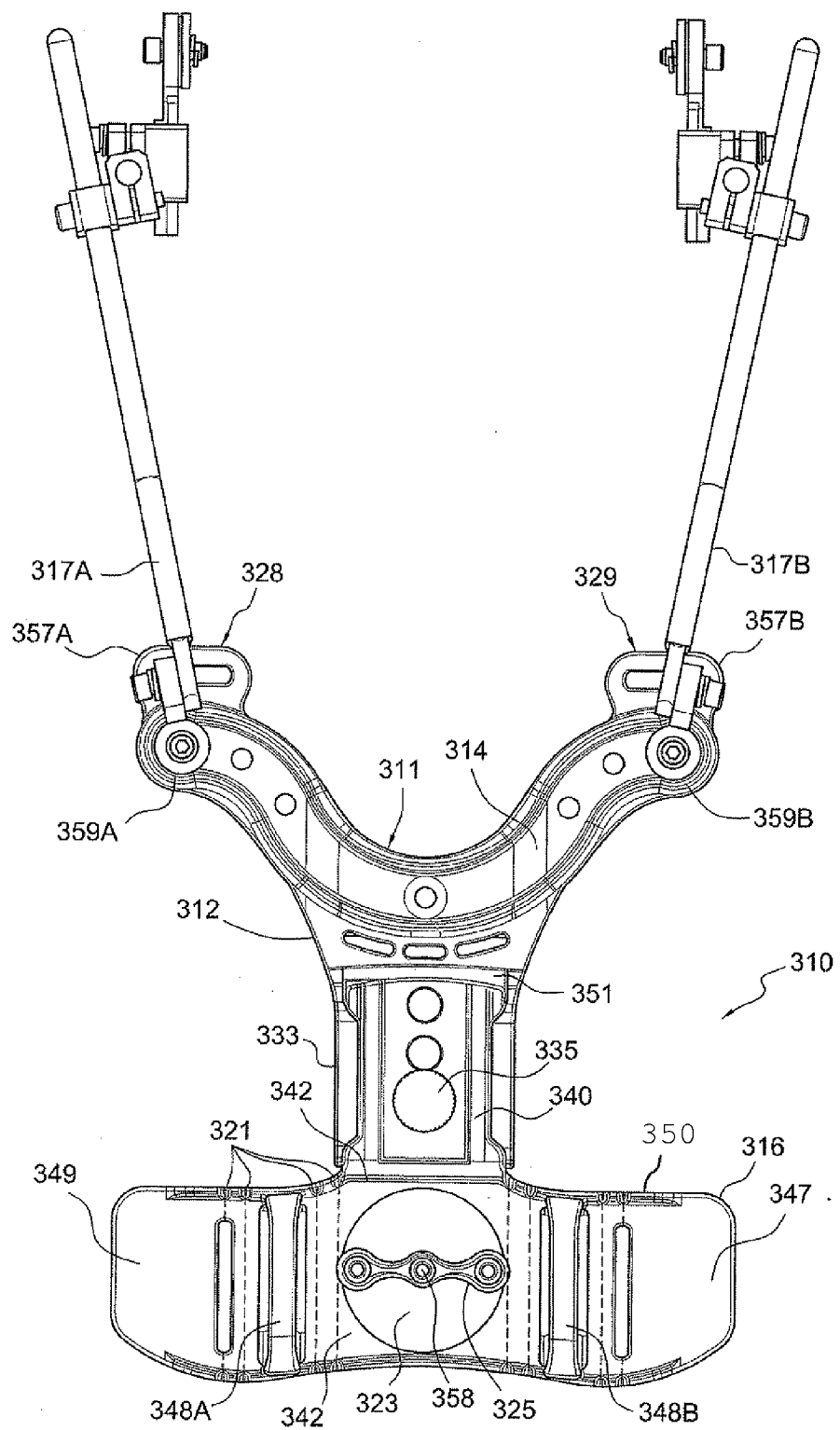
FIG. 1B is a front elevational view showing a variation of the anterior component according to FIG. 1A.

As shown in FIG. 1B, the first and second anterior rods 317A, 317B of the halo support secure to the first and second end areas 359A, 359B at anterior locations positioned below the first and second anterior tabs 357A, 357B. Moreover, the halo support has first and second posterior rods securing to first and second end areas of the posterior component at posterior locations below posterior tabs or wings. The anterior location whereat the first and second anterior rods secure is generally located at the same height on a wearer as the posterior location whereat the first and second posterior rods secure.

According to a variation, the first and second anterior rods 317A, 317B extend upwardly from the top component 311 in alignment with the anterior tabs 357 such that the first and second rods 317A, 317B extend past the anterior tabs 357 within a width of the first and second anterior tabs. This configuration provides for improved stability of the support rods and further more effectively distributes any forces on the wearer's chest.

Returning to FIG. 1 B, the anterior component 310 also defines portions contoured to a shape of a human abdominal region. The bottom component 316, connecting to the top component 311 via knob 335 and centrally located strut segment 340, forms living hinges 321 located on a lip portion 350 near corresponding first and second belt loops 348A, 348B. The lip portion 350 protrudes from and extends along the upper and lower edges of a periphery of the bottom component 316. It is noted that these living hinges may be similarly shaped to the living hinges 126 depicted in FIG. 6.

Figure 2C:
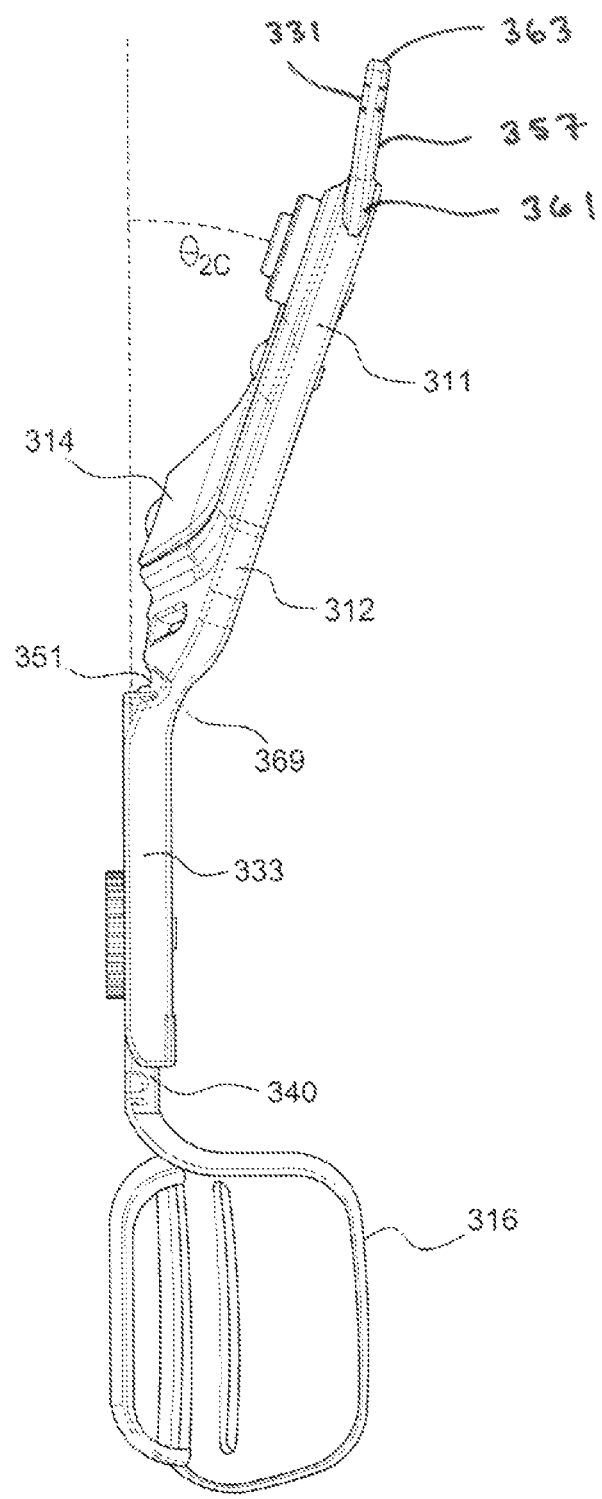
FIG. 2C is a side elevational view showing a variation of the anterior component according to FIG. 1B.
Figure 2D:
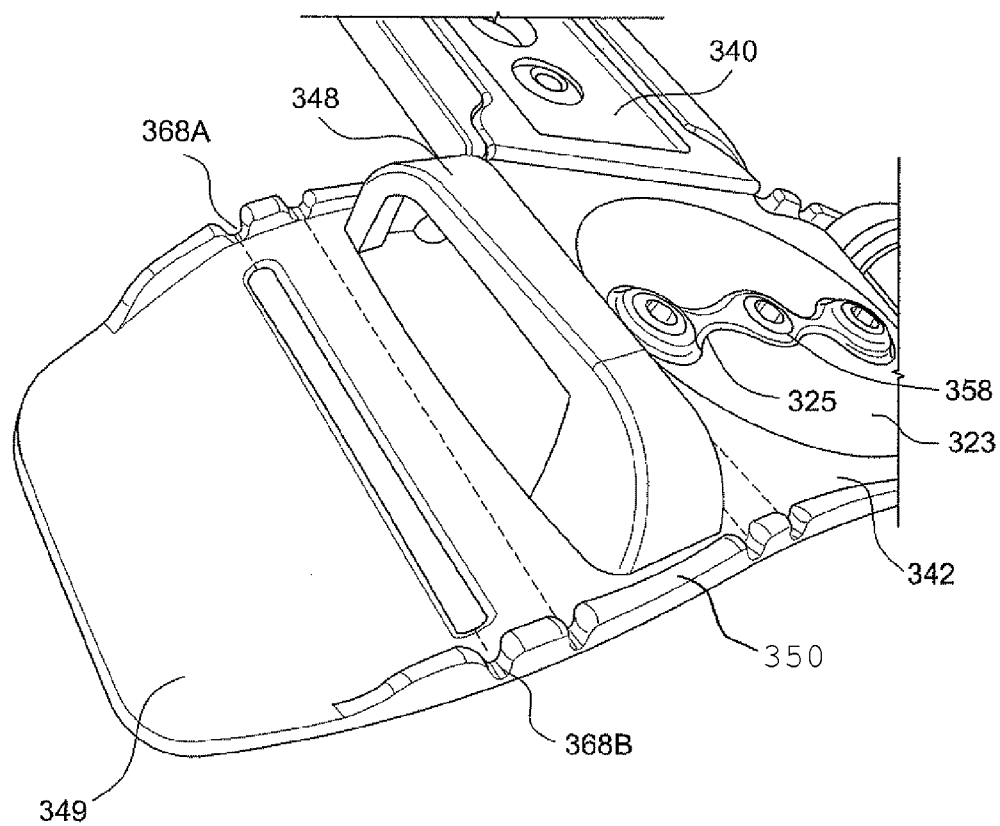
FIG. 2D is a perspective sectional view showing the anterior bottom component according to FIG. 1B.

FIGS. 1B and 2D show that the first and second living hinges 321A, 321B are biased so as to facilitate drawing the first and second opposed sides 347, 349 of the bottom component depending from the central lower region 342 inwardly toward one another and against a wearer's abdominal region thereby effectively distributing any forces exerted on the wearer's abdominal region. The hinges 321A, 321B are defined at least in part by opposed indentations 368A, 368B formed along the upper and lower edges of the periphery of and extending a thickness into the bottom component 316 from the outer surface of the bottom component 316.

The first and second living hinges are formed generally in vertical alignment with the first and second belt loops. The living hinges may be arranged so as to be located between the central lower region and the belt loops, and additional between the belt loops and end portions of the corresponding wings.

The bottom component 316 forms a series of locking apertures 358 formed on the central lower region 342 that are arranged to receive a locking device which secures lower strap stabilizers, as shown in FIG. 10, to the anterior component. The central lower region 342 defines a recessed portion 323 and raised sections 325 extending across the central lower region 342 whereat the locking apertures 358 are formed. The raised sections 325 allow for alignment of the strap stabilizers so as to better secure to the bottom component 316.

It will be pointed out that the top and bottom components 311, 316 may be couple via a locking device 335, as depicted in FIG. 2B. This locking device is preferably a rotatable dial having a threaded fastener that engages a threaded aperture formed along the bottom component 316.

The top component 311 and the bottom component 316 may be arranged to extend obliquely relative to one another. Specifically, in the variation of FIG. 2B, the upper portion 312 extends inwardly at a transition point 351 toward a wearer at an oblique angle relative to the attachment portion 333. In this variation, the transition portion 51 is a living hinge particularly biased at angle $\Theta_{2C}$ to favor extending toward the wearer's chest, while not only limited to extending in such direction; it may also flex outwardly from the wearer's chest. This variation permits a variety of angles which may be formed between the upper portion.

In a variation of the top component 311 shown in FIG. 2C, the upper portion 312 extends inwardly relative to the attachment portion 333 at a rigid transition point 369. The upper portion 312 is arranged at a predetermined angle $\Theta_{2C}$ at the transition point 369 relative to the attachment portion. According to this arrangement, the material forming the top component 311 may be reformed by subjecting it to elevated temperatures to individually fit the top component to the specific anatomy of an individual wearer.

Figure 3:
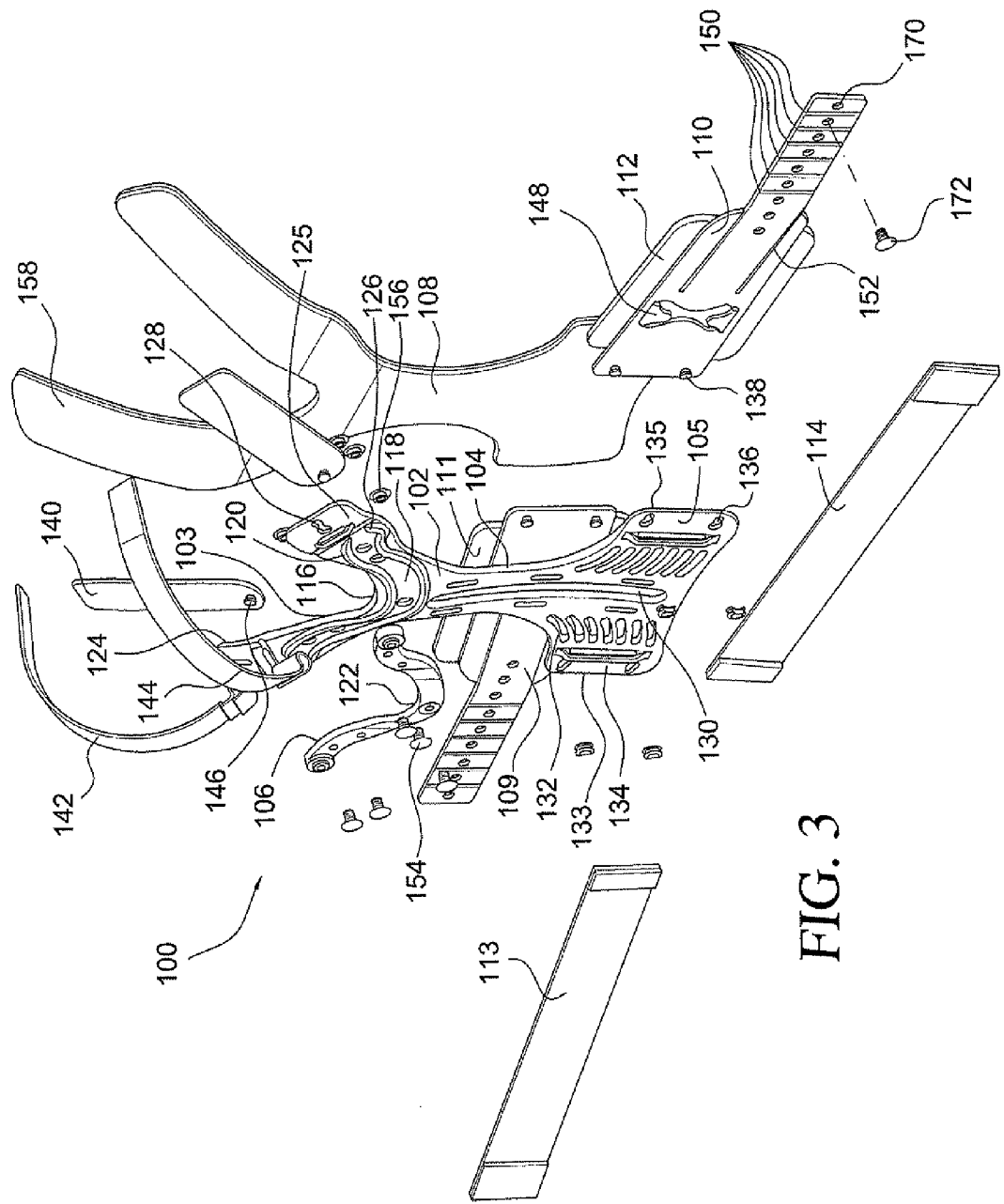
FIG. 3 is an exploded perspective view of a posterior component assembly according to an embodiment of the invention.
Figure 4:
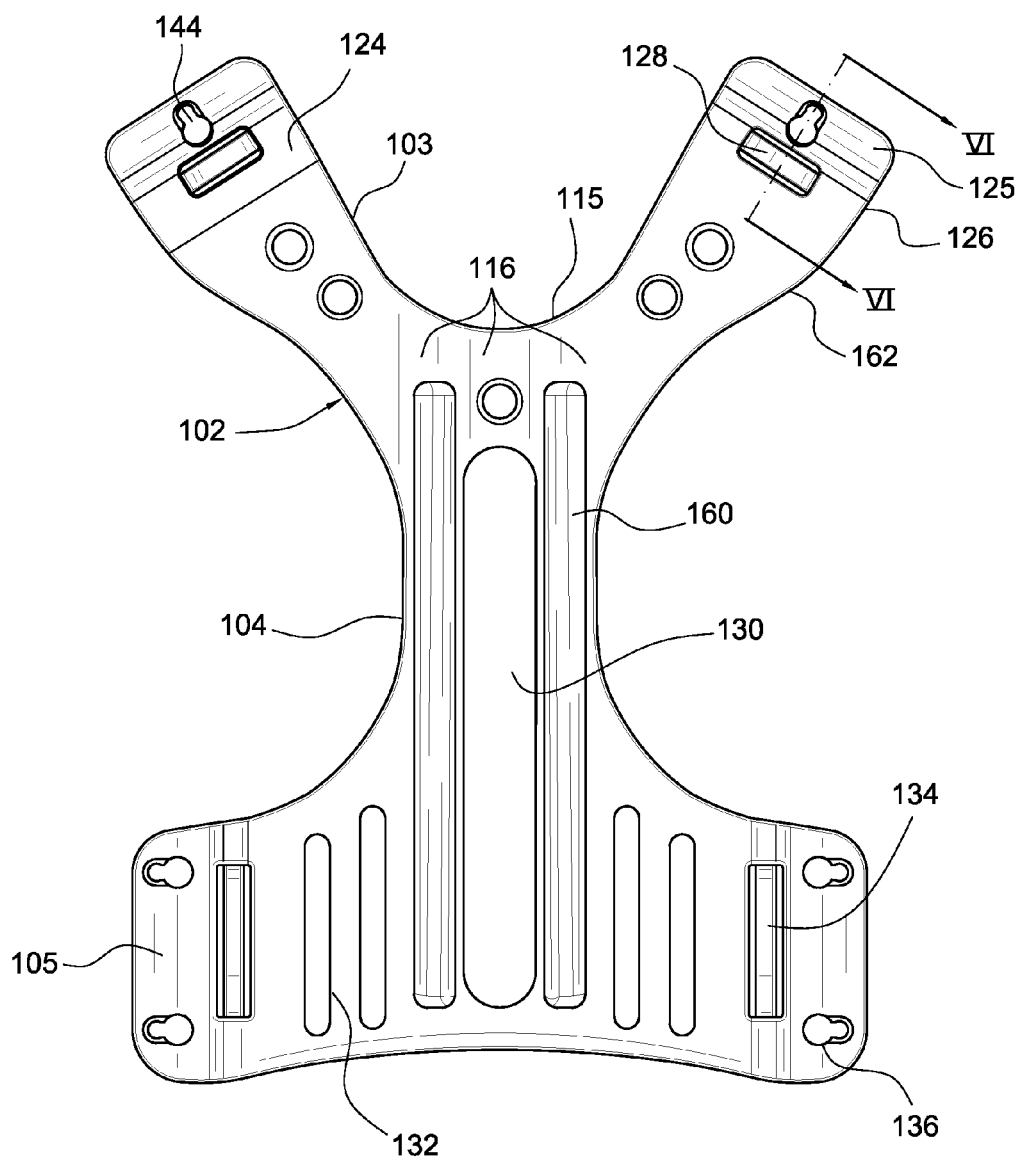
FIG. 4 is an elevational view of a variation of the posterior component according to FIG. 3.
Figure 5:
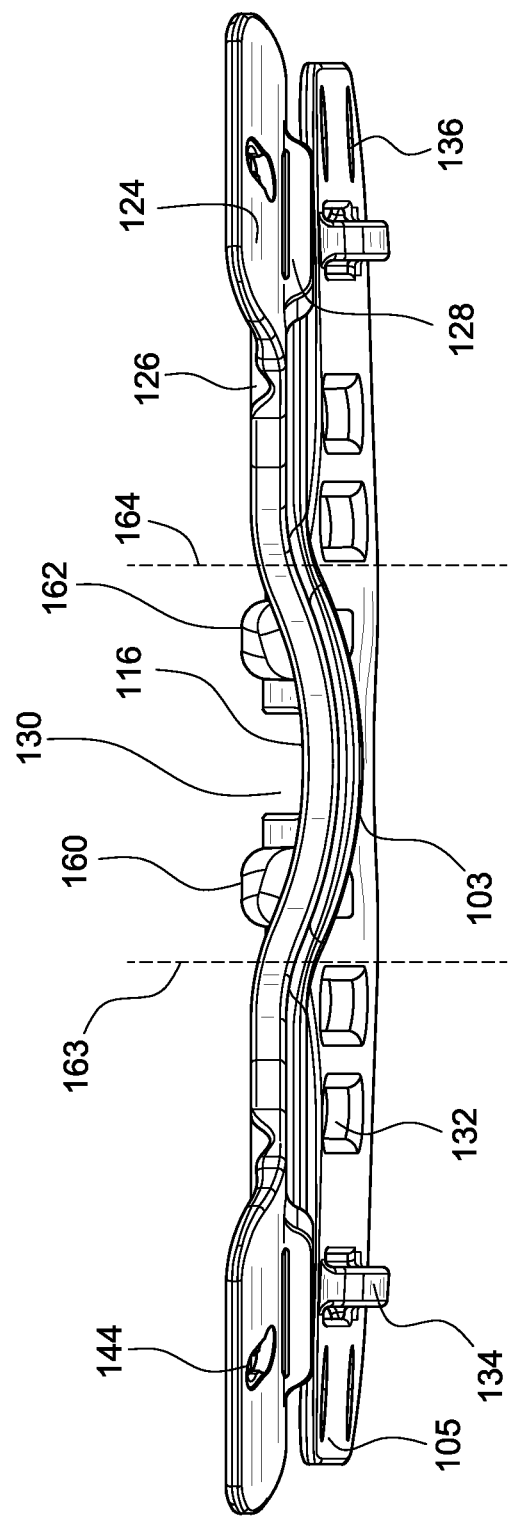
FIG. 5 is a top plan view of the posterior component according to FIG. 4.

Turning to the posterior vest assembly, FIGS. 3-5 depict an embodiment of a posterior vest assembly 100. The posterior vest assembly includes a posterior component 102 having upper, middle and lower portions 103, 104, 105. As with the anterior top component 11, an interface plate 106 secures to the upper portion 103, and provides a means to secure the upright assembly. Likewise, padding 108 is secured to an inner surface of the posterior component 102.

In a similar manner to the anterior top component 11, the posterior component 102 defines an outwardly bowed portion 116 generally confined to the upper portion 103. The outwardly bowed portion 116 is defined generally in a vertical direction along the vertical centerline at the upper portion 103. The posterior component 102 has a generally curved configuration through the upper, middle and lower portions corresponding to a wearer's back. The bowed portion 116 is generally three-dimensional in relation to remainder surfaces or regions comprising the remainder of the posterior component.

Again, in another similarity to the anterior top component, a segment of the periphery of the posterior component 102 at the upper portion 103 defines an arcuate profile 115 and extends downwardly towards the middle portion 104. The upper portion 103 forms wings 124, 125 located on opposed sides of the arcuate profile 115. The wings 124, 125 each define a living hinge 125, loops 128, and locking elements 144 for securing and guiding suitable straps for connecting to the top component of the anterior vest component assembly.

Figure 6:
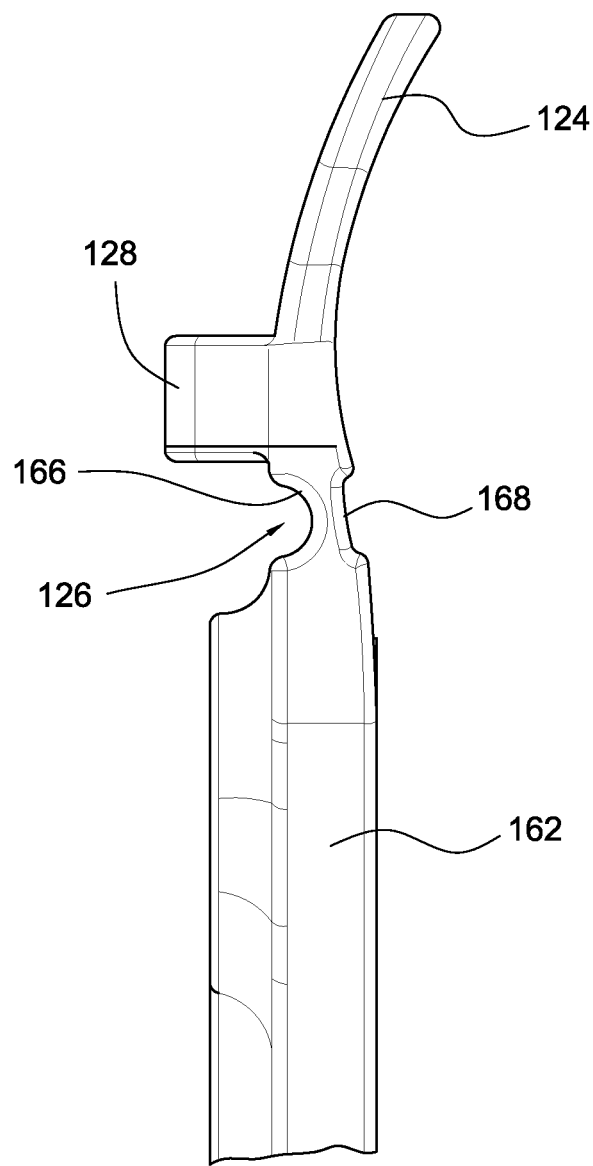
FIG. 6 is a sectional view taken along line VI-VI in FIG. 4.

In reference to FIG. 6, the living hinge 126 includes frontal and rear indentations 166, 168, respectively, which permit the hinge 126 to flex both outwardly and inwardly toward the wearer. The living hinge 126 is particularly advantageous to permit some movement or adjustability of the wings 124, 125 since the posterior component is either rigid or semi-rigid. The flexure of wings 124, 125 provided by the living hinge 126 therefore permits a more conforming fit about the shoulder when the straps connecting to the wings 124, 125 are tensioned. This leads to more secure and comfortable fitting of the immobilization device on the wearer.

The upper portion 103 also defines a curvilinear recess 118 having an outwardly extending lip 120 located along portions of the periphery thereof, and extending between wings 124, 125 formed on opposed sides of the upper portion 103. The interface plate 106 fits securely within the recess 118, and corresponds therewith in shape. Both the interface plate 106 and the recess 118 have outwardly bowed portions 122, 123, which correspond in location and shape to the outwardly bowed portion 116. Suitable fastening elements 154, 156 are used to secure the interface plate 106 to the posterior component 102.

The posterior component 102 defines an elongate opening 130, which is located along the centerline of the posterior component and generally corresponds to the spinal column of a wearer of the immobilization device. In addition, the posterior component 102 forms a plurality of ventilation slots 132, which facilitate circulation of air between the posterior component and the wearer.

The posterior vest assembly 100 includes padding elements 160, 162 extending along the spinal column and generally conforming to the shape of the posterior component. In particular, the padding elements 160, 162 extend at least in part into the outwardly bowed portion 116 located at the upper portion of the posterior component 102. Additionally, the padding elements 160, 162 extend along portions alongside the opening 130.

The padding elements 160, 162 are provided to minimize any pressure that may be exerted against the wearer by the immobilization device along the spinal column of the wearer. Indeed, the padding elements 160, 162 fall within the confines 163, 164 of the outwardly bowed portion 116, so as to provide cushioning within this region, and effectively minimize any pressure loads against the spinal column of the wearer.

Turning to the lower strapping system for securing the posterior vest assembly 100 to the anterior vest assembly 10, the lower portion 105 of the posterior component 102 defines lower lateral wings 133, 135 protruding outwardly relative to the centerline of the posterior component. The lower strapping system also includes bendable strap stabilizers 109, 110 having locking elements 138 and connect to locking slots or keyholes 136 formed on the lateral wings 133, 135. The lower strapping system further includes elastic straps 113, 114 that secure to belt loops 134 formed on the lateral wings 133, 135, and overlie on an outer surface of the strap stabilizers 109, 110. Suitable padding 112 is connected to an inner surface of the strap stabilizers 113, 114 and adjacently faces the wearer.

The strap stabilizers 109, 110 are more rigid and have a greater height than the elastic straps 113, 114. The height of the strap stabilizers 109, 110 provides a greater coverage over the wearer than the elastic straps 113, 114. This configuration allows for improved distribution of pressure about the wearer, and a more stable support about the wearer. The strap stabilizers define retention elements 148 which maintain the elastic straps 113, 114 over the strap stabilizers 113, 114, assure that they do not drift over areas of the wearer that are not covered by the strap stabilizers 113, 114.

Figure 7:
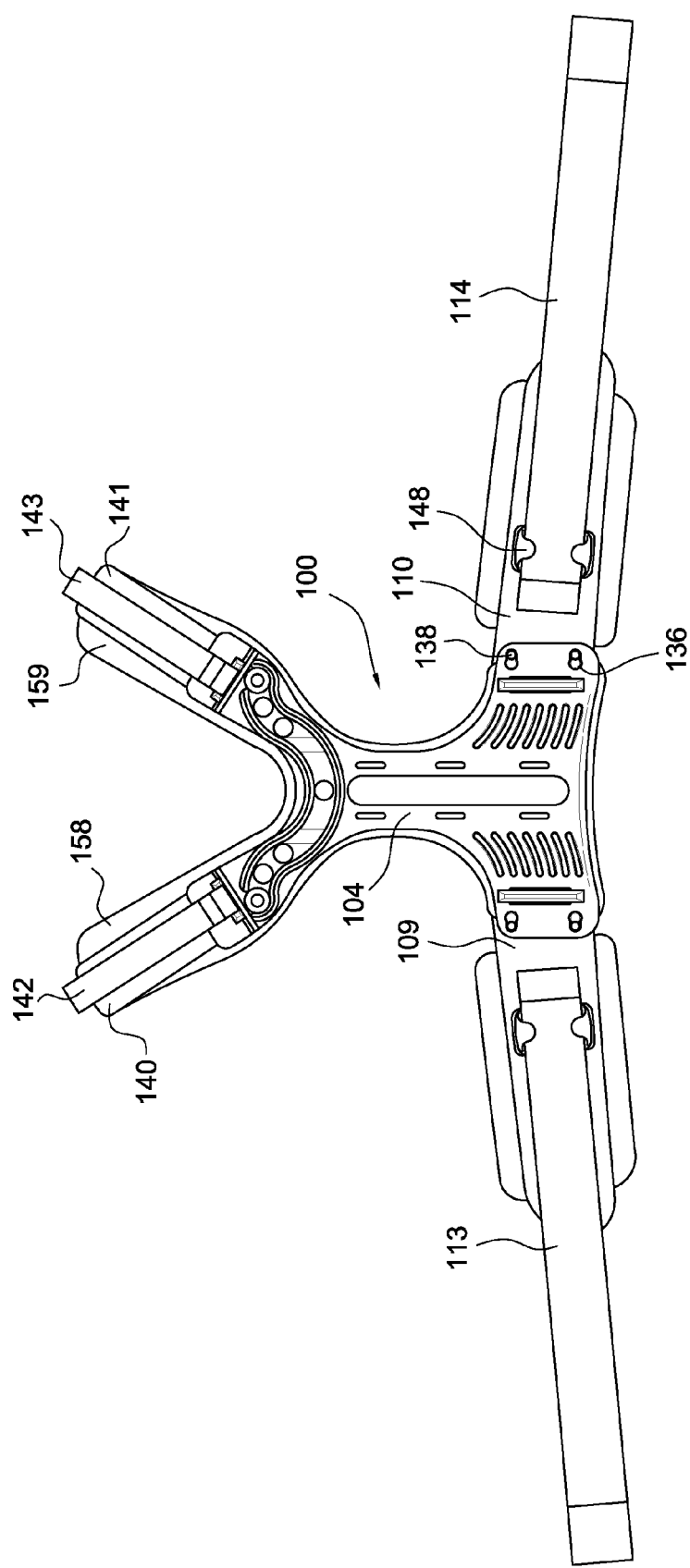
FIG. 7 is schematic view of the posterior vest assembly according to FIG. 3A.

In referring to FIG. 7, the strap stabilizers 109, 110 are connected to the posterior component 104. The strap stabilizers 109, 110, and elastic straps 113, 114 are arranged to extend about the wearer and through the belt loops 48 on the anterior component 11.

According to one variation, the strap stabilizers 109, 110 each define a plurality of apertures 170 which may be fixably secured via an affixation element 172, which couples an aperture 170 on both strap stabilizers 109, 110 to the affixation point 58, located on the anterior component 11. Alternatively, the strap stabilizers 109, 110 extend through the belt loops 48 on the anterior component 11 without any particular and direct affixation to the anterior component 11. Instead, the elastic straps 113, 114 connect to one another (via, for example, hook and loop fasteners) and secure the strap stabilizers 109, 110 via pressure exerted thereover. This variation provides for a more flexible fit, and allows for an ease of attachment of the immobilization device onto the wearer.

In addition to the aforementioned features of the strap stabilizers, the strap stabilizers 109, 110 define trim lines 150 at selected locations, which permit the sizing of the strap stabilizers to the girth of the wearer. Also, each strap stabilizer 109, 110 defines separation lines 152 which allow for portions of the strap stabilizers corresponding to the elastic straps to better conform to wearer when the elastic straps are tensioned. The separation lines 152 have the particular advantage of enabling a base portion of the strap stabilizers connecting to the posterior component to remain more rigid and/or robust, which portions of the strap stabilizers corresponding to the elastic straps with greater flexibility.

The upper strapping system also includes sections particularly arranged for securing the posterior vest assembly to the anterior vest assembly over the shoulders. Specifically, the upper strapping system includes strap stabilizers 140, 141 that attach to the wings 124, 125 in a similar manner, as do the strap stabilizers 109, 110 to the lateral wings 133, 135. Further, straps 142, 143 overlie an outer surface of the strap stabilizers 140, 141 in a similar manner, as do the elastic straps 113, 114 over the strap stabilizers 109, 110. The straps 142, 143 couple to corresponding loops 31 of the anterior component 11. However, the strap stabilizers 140, 141 may extend only over part of the shoulder of the wearer or completely over the shoulder of the wearer and secure to the loops 31 on the anterior component 11. Suitable padding 158, 159 underlie the inner surface of the strap stabilizers 140, 141 so as to provide additional comfort to the wearer.

Figure 8:
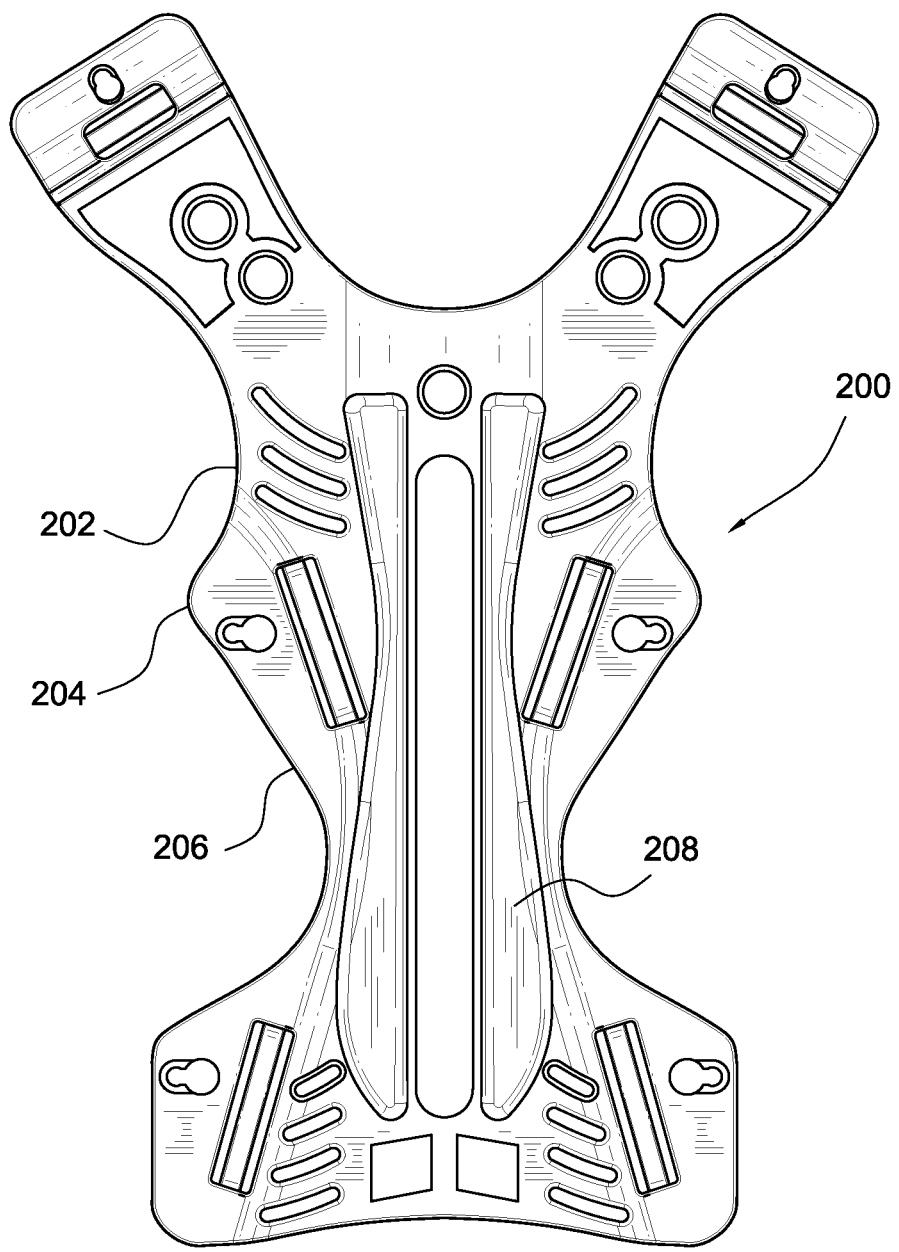
FIG. 8 is an elevational view of another variation of the posterior component.

In referring to FIG. 8, another variation of the posterior component 200 is depicted. This variation of the posterior component 200 is particularly designed to accommodate a wearer having a longer back. The posterior component 200 includes many of the same features as the posterior component 102. However, this posterior component 200 includes vertically curved contours on the side periphery thereof including sections 202, 206 located between laterally protruding section 204. Additionally, elongate pads 208 are secured to the inner surface of posterior component 200 and generally correspond to the geometry thereof.

Figure 9:
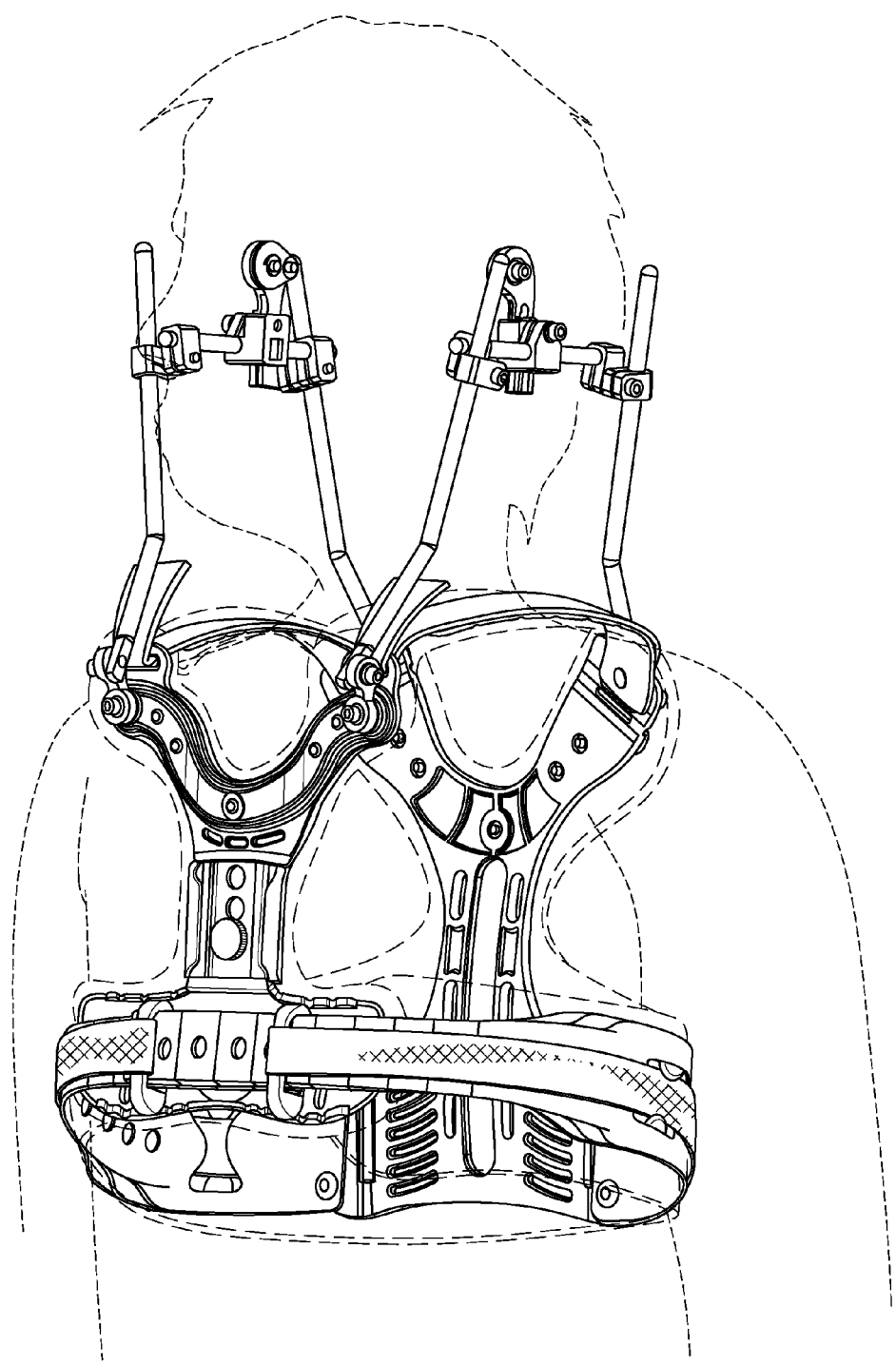
FIG. 9 is an assembly view showing an immobilization device having the anterior component according to FIG. 1B and the posterior component according to FIG. 3.

FIG. 9 exemplifies the immobilization device on a wearer with the anterior vest assembly of FIG. 2B and the posterior component of FIG. 7 in combination with the strapping systems according to FIG. 3.

While the foregoing embodiments have been described and shown, it is understood that alternatives and modifications of these embodiments, such as those suggested by others, may be made to fall within the scope of the invention.

The invention claimed is:

1. An immobilization device, comprising:
a rigid or semi-rigid anterior component having opposed inner and outer surfaces and defining portions arranged to contour to a shape of a lower chest or abdominal region, the anterior component having a bottom portion defining a central lower region having first and second opposed sides, the first and second sides of the central lower region forming first and second belt loops, respectively, protruding outwardly from the bottom portion and first and second wings, respectively, extending from beyond the corresponding first and second belt loops, a lip portion on the outer surface protruding from and extending along the upper and lower edges of a periphery of the central lower region, the central lower region forming first and second living hinges located near the corresponding first and second belt loops, the first and second living hinges are formed by opposed indentations located along the lip portion and extending a thickness into the bottom portion from an outer surface of the bottom component, the first and second living hinges biased so as to facilitate drawing the first and second opposed sides of the central portion inwardly toward one another and against a wearer's abdominal region;
a posterior component defining portions contoured to a shape of a human back; and
a strapping system connecting the posterior component to the central lower portion of the anterior component.

2. The immobilization device according to claim 1, wherein the first and second living hinges are formed generally in vertical alignment with the first and second belt loops, respectively.

3. The immobilization device according to claim 1, wherein the first and second living hinges are each located on a first side of the first and second belt loops adjacent the central lower region.

4. The immobilization device according to claim 3, further comprising third and fourth living hinges located between the first and second belt loops and end portions of the first and second wings, respectively.

5. The immobilization device according to claim 1, wherein the strapping system includes first and second elongate strap stabilizers mounted on the posterior component, the anterior component forming at least one locking aperture formed on the central lower region, a locking device securing the strap stabilizers to the anterior component engaging the locking aperture.

6. The immobilization device according to claim 5, wherein the first and second strap stabilizers extend over the first and second wings, respectively and urge the first and second wings inwardly at least at the first and second living hinges.

7. The immobilization device according to claim 1, wherein the first and second living hinges further include opposed indentations on the inner surface and extending a thickness into the bottom portion from an inner surface of the bottom component, the first and second living hinges biased so as to facilitate drawing the first and second opposed sides of the central portion outwardly toward one another and away from a wearer's abdominal region.

8. An immobilization device, comprising:
a rigid or semi-rigid anterior component including a two-dimensional shaped section contoured to a shape of the human chest, the anterior component forming an anterior outwardly bowed area relative to the two-dimensional shaped anterior section and corresponding to the sternum of the wearer, the anterior component including a top component and a bottom component having a central strut segment extending in a substantially vertical configuration, the top component having a substantially vertical attachment portion slidably engaging the bottom component, the top component defining an upper portion extending inwardly at a transition point toward a wearer at an oblique angle relative to the attachment portion;
the transition point is a living hinge formed by a generally horizontal indentation located along a surface of the top component that biases the upper portion among a plurality of angles relative to the attachment portion at least in the direction toward a wearer's chest.

9. The immobilization device according to claim 8, further comprising:
a posterior component including a two-dimensional shaped section contoured to a shape of the human back; and
a strapping system connecting the anterior and posterior components.

10. The immobilization device according to claim 8, wherein the bottom component defines opposed first and second wing portions each having at least one living hinge, the wing portions bendable at the at least one living hinge to bend toward the abdomen of the wearer.

11. The immobilization device according to claim 8, wherein the transition point rigidly directs the upper portion relative to the attachment portion.

* * * * *